(12) United States Patent
Cook et al.

(10) Patent No.: US 7,419,507 B2
(45) Date of Patent: Sep. 2, 2008

(54) ELBOW ARTHROPLASTY SYSTEM

(75) Inventors: James L. Cook, Columbia, MO (US); Jerry Lower, Bourbon, IN (US)

(73) Assignee: The Curators of the University of Missouri, Columbia, MO (US)

( * ) Notice: Subject to any disclaimer, the term of this patent is extended or adjusted under 35 U.S.C. 154(b) by 544 days.

(21) Appl. No.: 10/645,372

(22) Filed: Aug. 21, 2003

(65) Prior Publication Data
US 2005/0043806 A1 Feb. 24, 2005

(51) Int. Cl.
*A61F 2/38* (2006.01)
(52) U.S. Cl. .................................. 623/20.13
(58) Field of Classification Search ... 623/20.11–20.13, 623/FOR. 20
See application file for complete search history.

(56) References Cited

U.S. PATENT DOCUMENTS

| | | | | |
|---|---|---|---|---|
| 4,038,704 A | * | 8/1977 | Ring | 623/20.11 |
| 4,242,758 A | * | 1/1981 | Amis et al. | 623/20.11 |
| 5,041,117 A | | 8/1991 | Engelhardt | |
| 6,027,534 A | | 2/2000 | Wack et al. | |
| 6,162,253 A | | 12/2000 | Conzemius et al. | |
| 6,306,171 B1 | | 10/2001 | Conzemius | |

FOREIGN PATENT DOCUMENTS

| GB | 1 452 924 | * 10/1976 | 623/20 FOR |
|---|---|---|---|
| GB | 1 528 906 | * 10/1978 | 623/20 FOR |

OTHER PUBLICATIONS

2000 Annual Report, Comparative Orthopaedic Laboratory, University of Missouri, distributed Feb. 2001.

* cited by examiner

*Primary Examiner*—Dave Willse
(74) *Attorney, Agent, or Firm*—Senniger Powers LLP

(57) ABSTRACT

A prosthetic elbow for replacing an elbow of a dog or a human to restore normal, pain-free joint function. The elbow includes a humeral component for attachment to a humerus and a radioulnar component for attachment to an ulna. The humeral component includes a generally cylindric spool having a contoured external surface defining a first articular surface. The radioulnar component has a generally U-shaped contour with an inner peripheral surface defining a second articular surface sized and shaped for engagement with the first articular surface. Positional guides provide for implantation at precise locations.

16 Claims, 7 Drawing Sheets

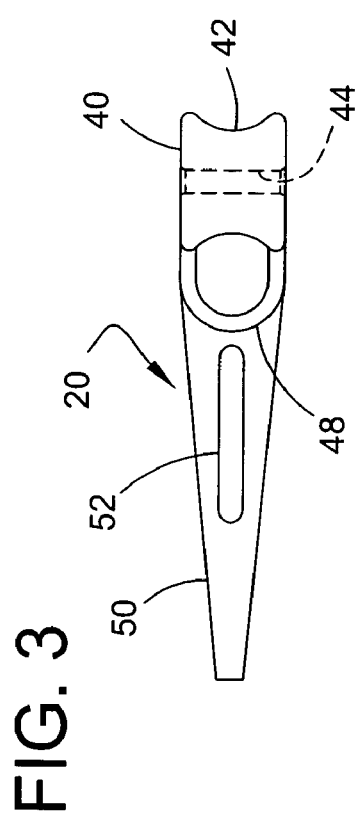
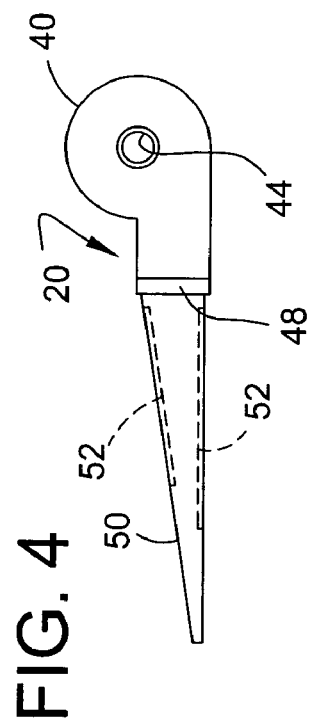
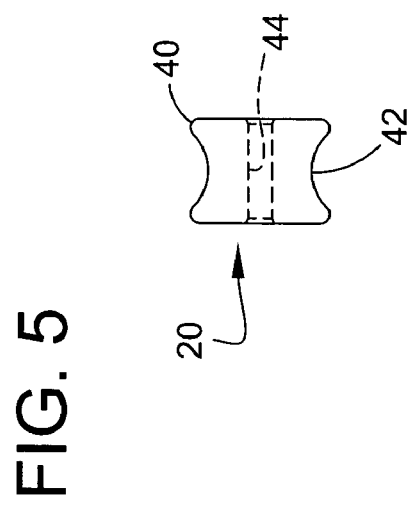
FIG. 3
FIG. 4
FIG. 5

ELBOW ARTHROPLASTY SYSTEM

BACKGROUND OF THE INVENTION

This invention relates generally to artificial joints, and in particular to a prosthetic elbow and technique for its implantation. Its primary use is with dogs or other animals, although it may also be applied to human beings.

Degenerative joint disease of an elbow, such as osteoarthritis, trauma, or dysplasia, can debilitate a dog. When nonsurgical treatments are no longer effective, a pet owner's only feasible options can be elbow arthrodesis (fusion of the joint), amputation, or euthanasia. Total elbow replacement for dogs is a promising alternative, but has not consistently resulted in an elbow retaining its normal, pain-free joint function over time. Moreover, the process of surgical implantation has been invasive, disrupting lateral collateral ligaments and requiring extensive soft tissue dissection. Consequently, function of the elbow is degraded and the duration of recovery is extended.

SUMMARY OF THE INVENTION

Among the several objects and features of the present invention may be noted the provision of an elbow arthroplasty system for replacing an elbow of a dog or a human; the provision of such a system which produces normal, pain-free joint function; the provision of such a system which is firmly secure; the provision of such a system having positional guides for implantation at selected locations; and the provision of such a system for implantation with minimal invasiveness to ligaments and soft tissue surrounding the elbow.

In general, a prosthetic elbow for attachment to a humerus and ulna of the present invention comprises a humeral component comprising a generally cylindric spool having a contoured external surface defining a first articular surface. A radioulnar component comprises a body having a generally U-shaped contour with an inner peripheral surface defining a second articular surface sized and shaped for engagement with the first articular surface and relative movement thereagainst. The body of the radioulnar component is configured for snap-fit attachment to the spool.

In another aspect, a prosthetic elbow of the invention is for attachment to a humerus and ulna. The prosthetic elbow comprises a humeral component comprising a generally cylindric spool having a contoured external surface defining a first articular surface. A radioulnar component comprises a body having a generally U-shaped contour with an inner peripheral surface defining a second articular surface sized and shaped for engagement with the first articular surface. The humeral component has a bore extending axially through the spool for receiving at least one fastener to attach the humeral component to the humerus. The humeral component is free of a stem for extending into a medullary canal of the humerus.

Other objects and features of the present invention will be in part apparent and in part pointed out hereinafter.

BRIEF DESCRIPTION OF THE DRAWINGS

FIGS. 3-5 are front, side, and end views of the humeral prosthesis of FIG. 1;

Corresponding reference characters indicate corresponding parts throughout the views of the drawings.

DETAILED DESCRIPTION OF THE PREFERRED EMBODIMENT

Figure 1:
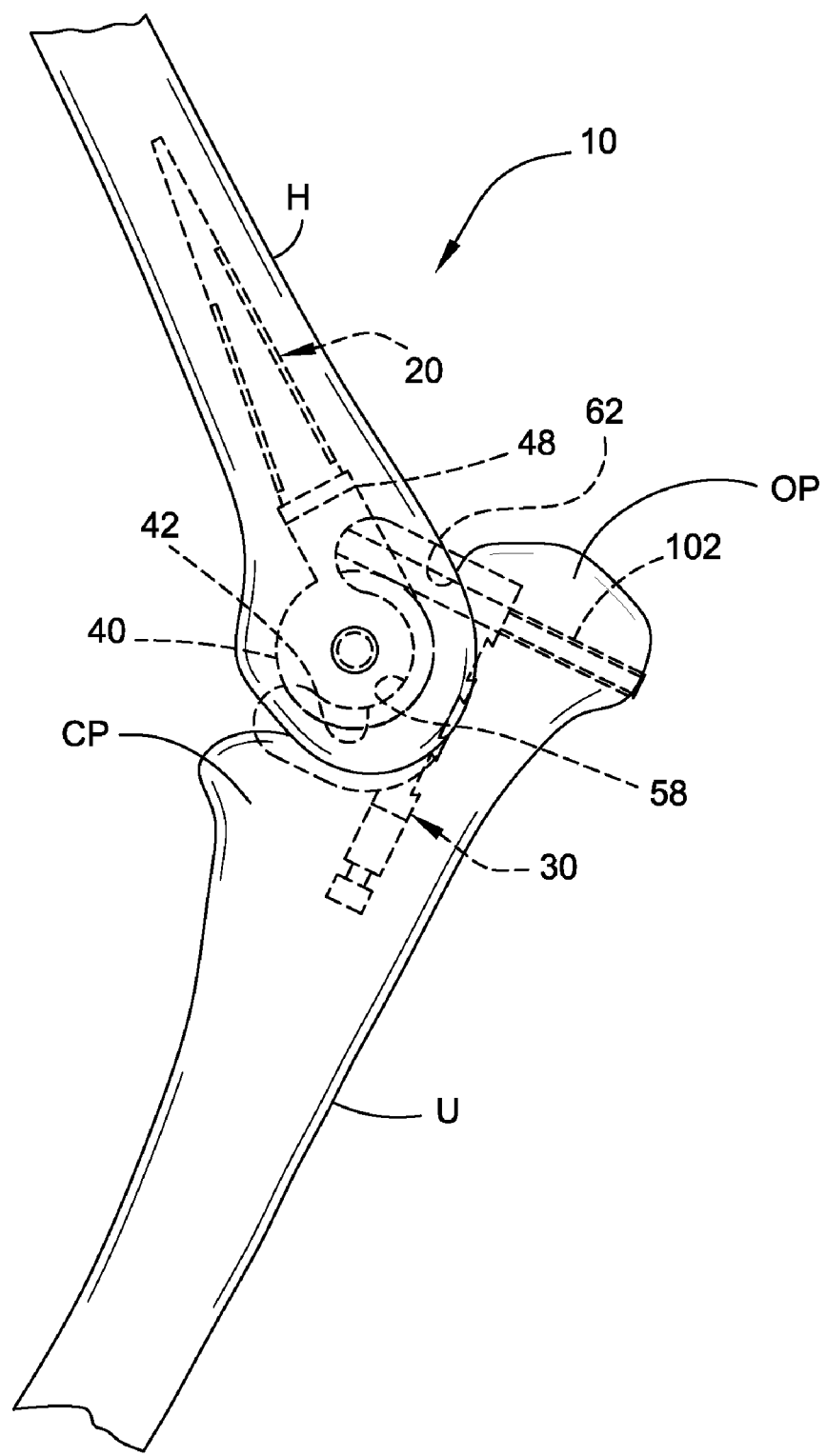
FIG. 1 is a side elevation of a humerus and ulna of a dog's elbow with prostheses according to the present invention.

Referring now to the drawings and in particular to FIG. 1, an elbow arthroplasty system according to the present invention is indicated generally at 10. The system 10 includes a humeral prosthetic component 20 for attachment to the humerus H and a radioulnar prosthetic component 30 for attachment to the ulna U. The reference numerals 20 and 30 designate their respective subjects generally.

Figure 2:
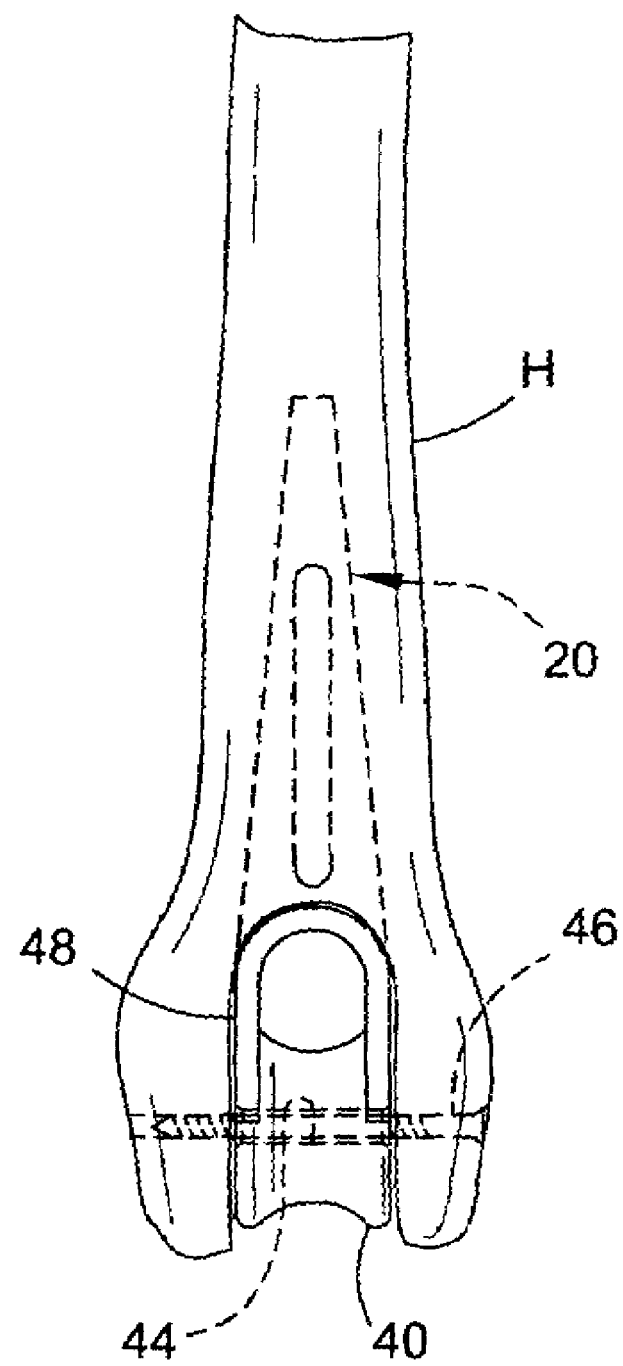
FIG. 2 is a rear elevation (caudal) of the humerus of FIG. 1.

The humeral component 20 includes a generally cylindric spool 40 (FIGS. 3-5) having a contoured external surface 42 providing a first articulating surface. The surface has a concave profile, similar to a trochlea of the humerus which is to be replaced. The spool 40 has a size which may be selected for the size of the dog and the particular joint. A bore 44 extends axially through the spool for receiving at least one fastener 46 (FIG. 2) to attach the humeral component to medial and lateral columns of the humerus. In one embodiment, the fastener 46 is a transcondylar screw. An arch-shaped bracket 48 integrally connected to the spool defines a cavity permitting rotational motion of the radioulnar component 30 around the spool with a portion of the radioulnar component being movable within the cavity. A stem 50 extends generally in a radial direction from the bracket 48, with the bracket connecting the stem and spool without obstructing motion of the radioulnar component relative to the spool. The stem tapers linearly to a narrow tip for insertion into the medullary canal of the humerus. Elongate, longitudinally extending depressions 52 (FIGS. 3 and 4) are positioned along the stem 50 to provide improved gripping by bone cement in the medullary canal. The humeral component 20 is made of a suitable material such as cobalt chrome, stainless steel, titanium, or a ceramic. It is secured to the humerus H in a suitable manner, such as by polymethylmethacrylate (PMMA) bone cement and the transcondylar screw 46 placed through the bore 44.

Figure 8:
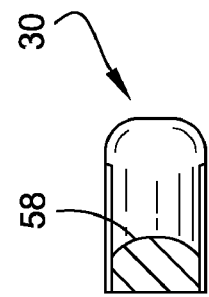
FIG. 8 is a section along line 8-8 of FIG. 6.
Figure 6:
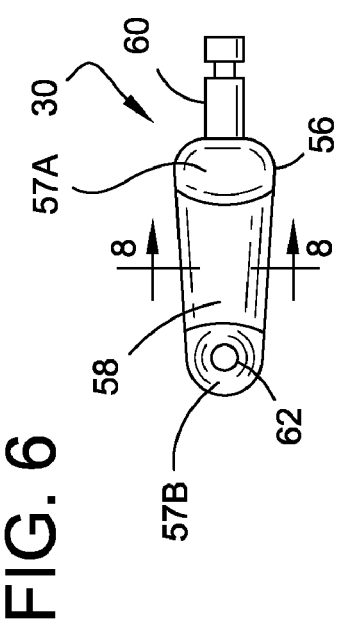
FIGS. 6 and 7 are front and bottom views of the radioulnar prosthesis of FIG. 1.
Figure 7:
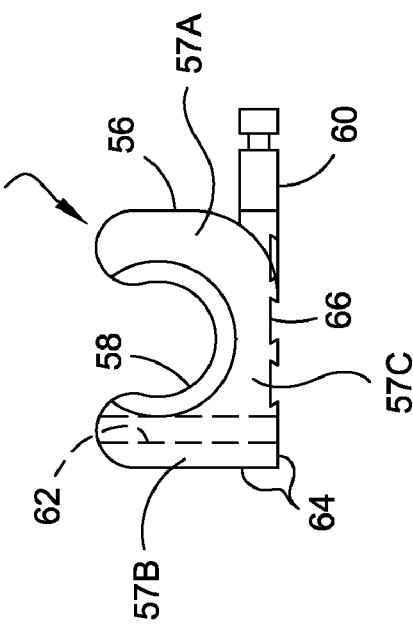

Referring to FIGS. 6-8, the radioulnar component 30 has a body 56 with spaced apart first and second arms 57A, 57B extending longitudinally outward from a base 57C. Together, the arms and the body define a generally U-shaped contour with an inner peripheral surface 58 defining a second articular surface. The second surface 58 is sized for engagement with the first articular surface 42 (FIG. 1) for cooperative relative movement, and it has a convex profile as shown in FIG. 8 which is received in the corresponding concave profile of the spool. A peg 60 extends generally transversely from the first arm 57A of the body 56 for being received into a bore formed in the proximal ulna for securement of the body and ulna. In addition, the body 56 includes a bore 62 extending longitudinally in the second arm 57B, generally orthogonal to the peg 60 for receiving a suitable fastener, such as an olecranon screw (not shown). PMMA bone cement may be distributed along the peg 60 and along outer peripheral surfaces 64. Notches as indicated at 66 or other roughened areas are included on the outer peripheral surfaces to facilitate ingrowth of bone for permanent attachment.

The body 56 of the radioulnar component 30 is configured for snap-fit attachment to the spool 40. The inner peripheral surface 58 comprises a circular arc extending circumferentially through a range at least as great as 180 degrees. Preferably, the range is greater than 180 degrees so that the body will effectively self-retain on the spool. In the illustrated embodiment, the range is about 230 degrees. The body 56 is made of a suitable flexible and resilient material, such as a high molecular weight polyethylene, so that the surgeon may deflect the body to install it on the spool. In one embodiment, the radioulnar component 30 is of one-piece construction. Snap-fit provides a reliable attachment and relative motion, without the need for fasteners or more time-consuming or complex connection. After implantation, a full range of motion of the prosthetic elbow from flexion to extension is between 135 and 140 degrees, which is an improvement on prosthetic elbows of the prior art (e.g., 127 degrees).

Figure 10:
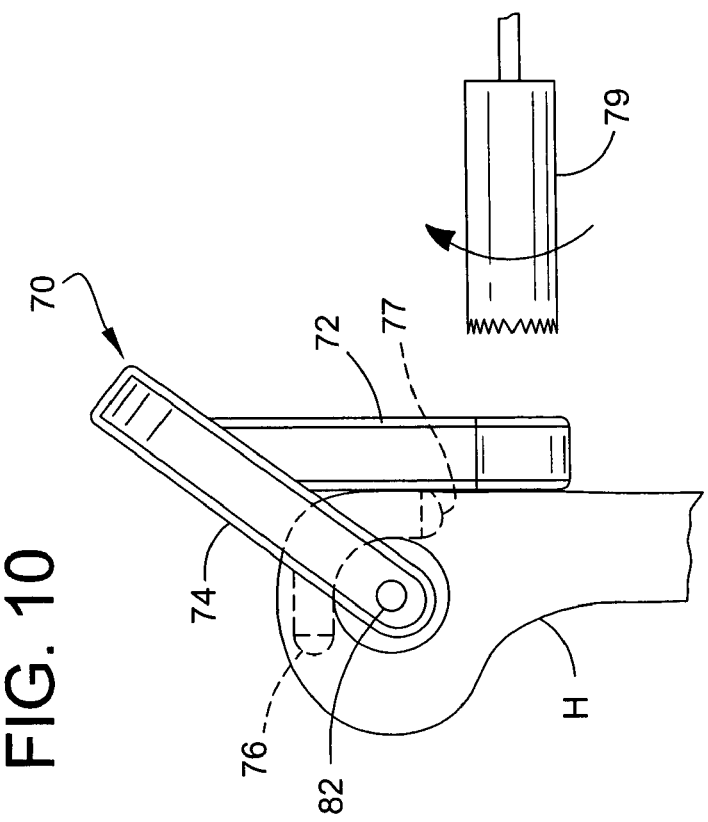
FIGS. 9 and 10 are rear and side views of a humeral cutting guide and a fragmentary portion of the humerus.
Figure 9:
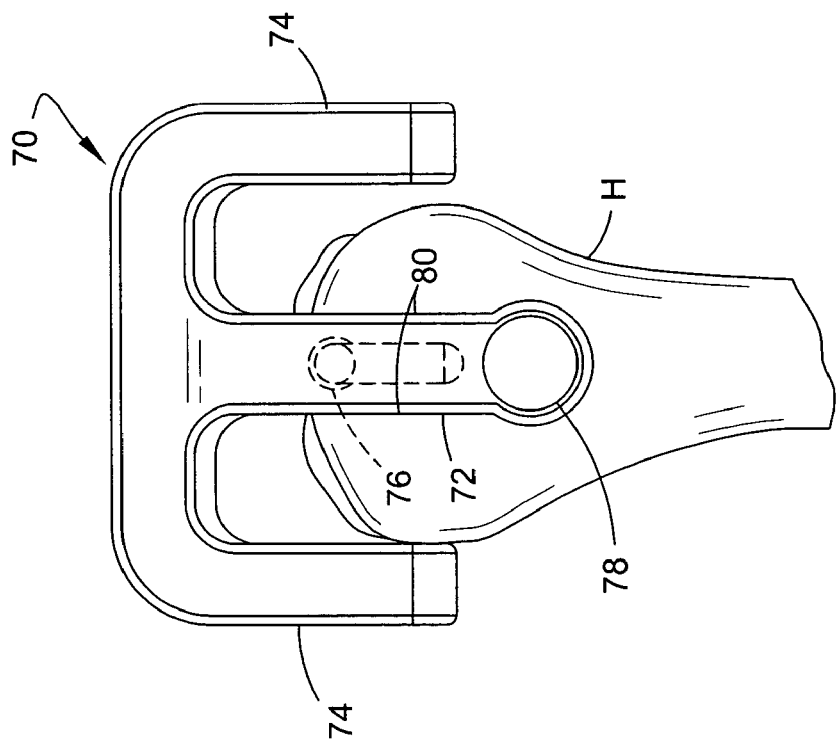

Positional guides (or "jigs") are provided to ensure that the replaced elbow restores an anatomical center of rotation of the joint, and thereby the bones and ligaments are maintained at the same relative positions before and after surgery over the elbow's range of motion. The guides also provide repeatability to the implantation and use of the system for several elbows. As shown in FIGS. 9 and 10, a humeral jig 70 is provided for locating the humeral component H. The jig 70 has three arms including a central arm 72 and two outer arms 74. The central arm 72 has two rounded pins 76, 77 which the surgeon aligns with the articular surface of spool-shaped cartilage on the humerus (i.e., the trochlea) to locate the jig. A hole 78 at the tip of central arm 72 defines a circular cutting guide for a surgical cutting tool, such as a trephine 79 (FIG. 10), which may be received through the hole. That cut edge will align and tangentially connect with straight cuts made along outer edges 80 of the central arm 72, so that diseased tissue may be removed. The two outer arms 74 have holes 82 defining an axis for locating and drilling a bore through the center of the humerus to properly position the transcondylar screw and spool. The size of the humeral jig is selected to correspond with a size of the spool which is sized according to the natural dimensions of the elbow.

Figure 11:
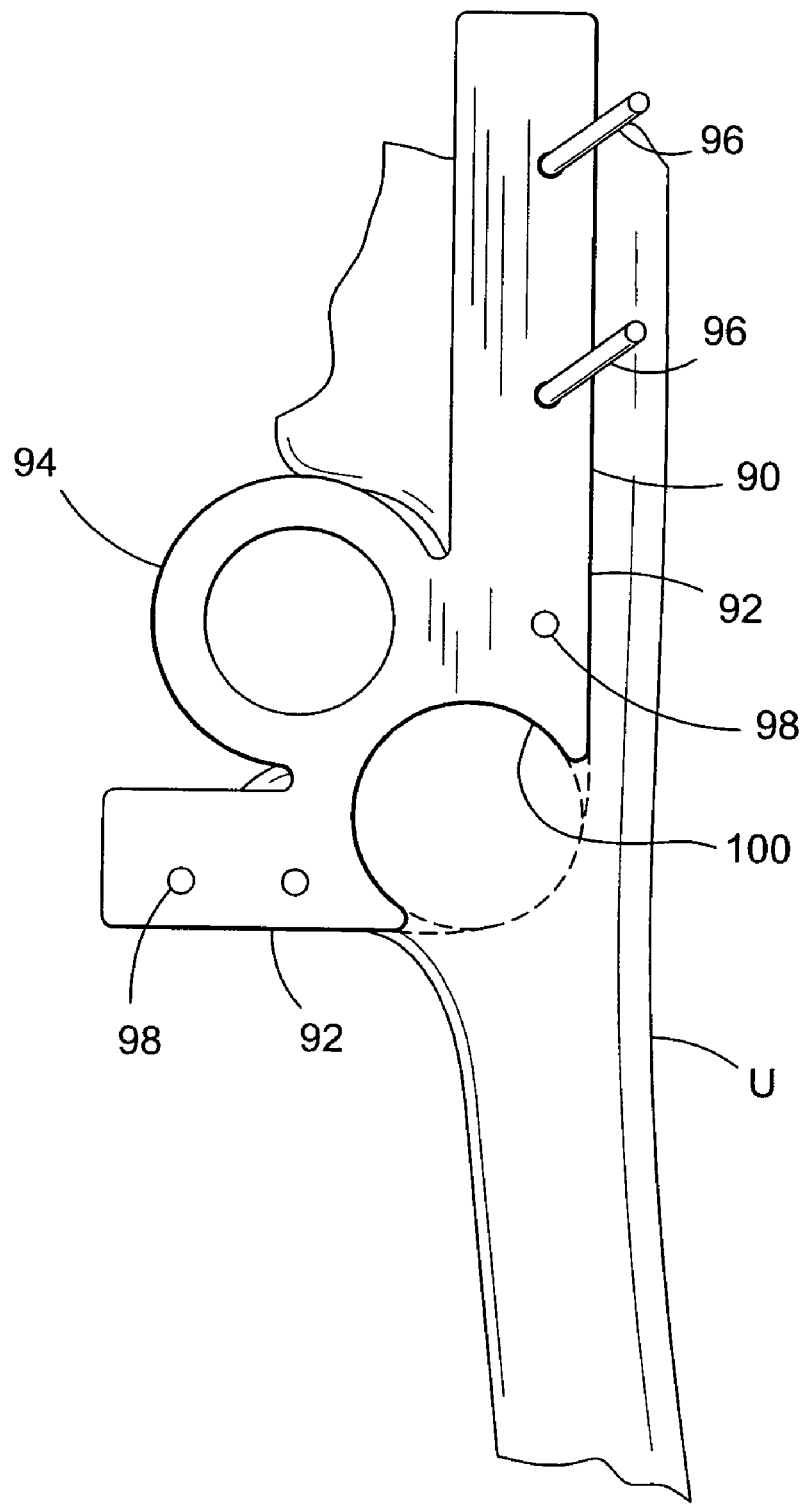
FIG. 11 is a side view of a radioulnar cutting guide and a fragmentary portion of the ulna.

Referring to FIG. 11, a radioulnar jig 90 is provided for locating the radioulnar component 30 (not shown in FIG. 11). The jig 90 has an L-shape with two outer edges 92 which are generally straight comprising cutting guides. An enclosed circle 94 is a visual guide for the surgeon, who aligns a center of the enclosed circle with the anatomical center of rotation on the ulna U. Pins 96 are then inserted through pin holes 98 and into the bone to hold the jig in fixed position on the ulna. Two straight cuts are made along edges 92. A semicircular cutout 100 is configured to receive trephine 79 to cut an arc which tangentially meets the straight cuts along the outer edges 92. By making the cut along an arc instead of two perpendicular straight cuts, stress concentrations are minimized.

A process for implanting the prosthetic elbow is now described. First, an incision is made along the lateral aspect of the forelimb, from mid-humerus to mid-ulna, to expose the triceps, elbow joint, and ulna. A screw (not shown) is inserted through the ulna and radius (not shown) to prevent relative motion between the ulna and radius, thereby making the elbow joint a true hinge joint. An olecranon osteotomy is then performed to allow retraction of the triceps and permit access to the elbow joint from the posterior aspect.

The anconeal process of the ulna is cut off to allow placement of the humeral jig 70 on the distal end of the humerus H. The humeral jig is aligned with the articular surface by aligning pins 76, 77 on the trochlea. A transcondylar screw hole is drilled using the aligned holes 82 of the jig. Cuts are made in the humerus along edges 80 and through hole 78 of the jig for removal of the diseased bone and cartilege. The distal end of the humerus then has a forked shape with a central opening with smooth edges and configured for receiving the humeral component 20.

The radioulnar jig 90 is then positioned on the joint, and cuts are made in the ulna as described above. The ulnar medullary canal is then drilled and reamed to allow for insertion of the peg 60 of the radioulnar component 30 and cement fill. Similarly, the humeral medullary canal is drilled and reamed. A screw hole 102 (FIG. 1) is drilled through the olecranon process OP of the ulna and tapped. PMMA bone cement is injected into the humeral canal, the stem 50 of the humeral component 20 is inserted, and the transcondylar screw 46 is installed to connect the spool 40 with the surrounding bone structure. Similarly, PMMA bone cement is injected into the ulnar canal, the radioulnar component 30 is inserted, and the olecranon screw is inserted. The body of the radioulnar component 30 is attached by snap-fit to the spool 40. To complete the surgery, a pin and tension band wire (not shown) are used to replace the olecranon process of the ulna and re-attach the triceps muscles. The joint capsule, fascia, subcutis, and skin are closed routinely, and a bandage is placed. The caudal approach to the elbow is minimally invasive, and allows the collateral ligaments to be maintained intact.

Figure 12:
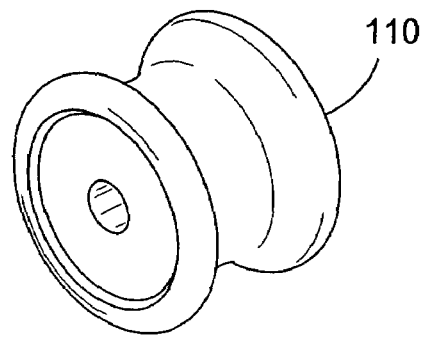
FIGS. 12-14 are perspectives of second, third, and fourth embodiments, respectively, of the humeral prosthesis.

A second embodiment 110 of the spool, shown in FIG. 12, has no stem for extending into the medullary canal of the humerus. The spool is "stemless" and is held in place by adjacent engagement with the medial and lateral columns of the humerus and by the transcondylar screw through its central bore. Advantages of this embodiment include elimination of the need to drill and ream the medullary canal of the humerus to fit the stem into the canal, reducing the risk of damage or fractures to the bone structure. Further, there is no need for left-hand and right-hand specific implants which can be needed for the stemmed design. The supratrochlear foramen provides a natural cavity adjacent the spool so that there is no need for the arched-shaped bracket 48, nor need to cut the semicircle using the hole 78 in the central arm 72 of the humeral jig 70.

Figure 13:
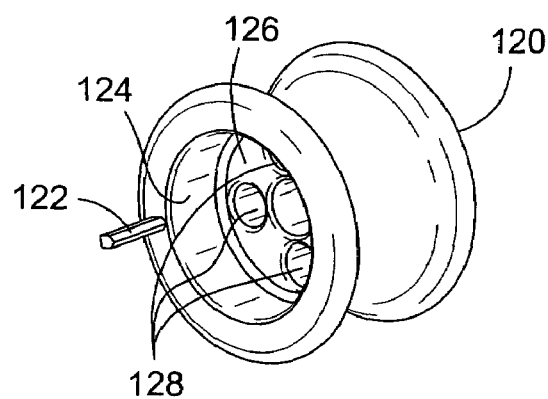

A third embodiment 120 of the humeral component (FIG. 13), also a "stemless" spool, has a peg 122 extending from the spool generally parallel to the axis of the spool. The peg 122 is for engaging the humerus and preventing rotation of the spool about the bore in the spool. A hole is drilled in the distal humerus to receive the peg. The spool of the third embodiment 120 also features a cavity 124 on its face to facilitate bone ingrowth and/or bone graft. The cavity 124 comprises a counterbore or chamfer in the face or edge of the spool, or at any location placed adjacent to bone. A sample of bone, such as an autograft bone replacement as known to those skilled in the art, may be placed in the cavity for grafting. A wall 126 of the cavity has holes 128 for passage of blood or growth of bone therethrough. The spool may have a second cavity (not shown) on its opposite face. The cavity 124 may be included with any stemmed or stemless spool embodiment. The cavity facilitates ingrowth of bone along the spool 40 to more permanently secure the spool to the humerus H, as loosening may otherwise occur over time at stressed areas of interface.

Figure 14:
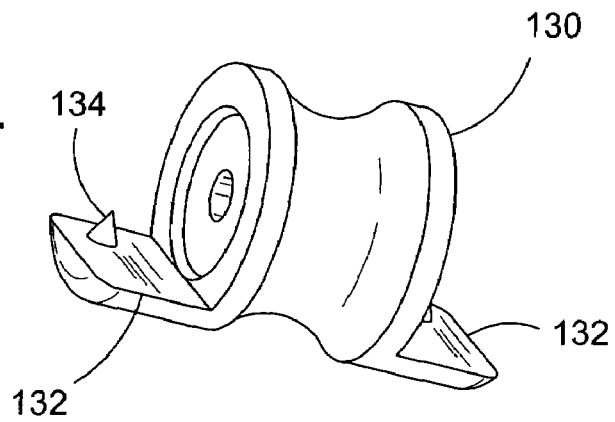

A fourth embodiment 130 of the humeral component (FIG. 14), also a "stemless" spool, has two generally flat panels 132 referred to as "wings". The panels extend from the spool in a generally axial direction, and are for engaging the humerus and preventing rotation of the spool 130 about the bore. A cleat 134 is positioned on each wing 132 for firmly fixing the position of the spool. An advantage of the fourth embodiment is that the wings cover and segregate arthritic cartilage adjacent to the spool which can otherwise continue to produce inflammation and pain.

In view of the above, it will be seen that the several objects of the invention are achieved and other advantageous results obtained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A prosthetic elbow for attachment to a humerus and ulna, the prosthetic elbow comprising:
    a humeral component comprising a generally cylindric spool having a contoured external surface defining a first articular surface, said spool being sized and shaped to fit within a recess cut between medial and lateral aspects of a condyle of the humerus;
    a radioulnar component comprising
        a body having base and a pair of spaced apart, first and second arms extending outward from the base, together defining generally U-shaped contour with an inner peripheral surface defining a second articular surface sized and shaped for engagement with the first articular surface and relative movement thereagainst, and
        a peg sized and shaped for being received in an axial bore in the ulna, the peg extending laterally outward from the first arm adjacent to the base,
        wherein the second arm of the body has a bore extending longitudinally therein in a direction generally orthogonal to the peg, the bore being sized and shaped for receiving a fastener inserted in an olecranon process of the ulna generally transverse to the longitudinal axis of the ulna to secure the radioulnar component to the ulna.

2. A prosthetic elbow as set forth in claim 1 wherein the inner peripheral surface of the radioulnar component comprises a bearing surface extending along a circular arc through at least about 180 degrees.

3. A prosthetic elbow as set forth in claim 2 wherein the radioulnar component is formed of a flexible and resilient material for snap-fit attachment of the spool to the radioulnar component.

4. In combination, a prosthetic elbow as set forth in claim 1 with humeral and radioulnar positional guides, each of the guides for locating surgical cuts to remove portions of a humerus and ulna to permit implantation of the respective components at locations for proper joint function, each of the guides configured for visual and anatomical alignment with the respective humerus and ulna for rotation of the prosthetic elbow about the physiological center of rotation of the natural elbow.

5. A prosthetic elbow as set forth in claim 1 further comprising a stem attached to the spool and extending generally radially therefrom, the stem configured for being received in a medullary canal of the humerus.

6. A prosthetic elbow as set forth in claim 1 wherein the humeral component has a bore extending axially through the spool for receiving at least one fastener to attach the humeral component to the humerus, the humeral component being free of a stem for extending into a medullary canal of the humerus.

7. A prosthetic elbow as set forth in claim 1 wherein the spool has a cavity for receiving bone.

8. A prosthetic elbow as set forth in claim 1 wherein the body of the radioulnar component is configured for snap-fit attachment to the spool.

9. A prosthetic elbow as set forth in claim 1 wherein the radioulnar component is adapted for attachment to both the ulna and an associated radius.

10. A prosthetic elbow for attachment to a humerus and ulna, the prosthetic elbow comprising:
    a humeral component comprising a generally cylindric spool having a contoured external surface defining a first articular surface;
    a radioulnar component comprising
        a body having base and a pair of spaced apart, first and second arms extending outward from the base, together defining generally U-shaped contour with an inner peripheral surface defining a second articular surface sized and shaped for engagement with the first articular surface and relative movement thereagainst, and
        a peg sized and shaped for being received in an axial bore in the ulna, the peg extending laterally outward from the first arm adjacent to the base,
        wherein the second arm of the body has a bore extending longitudinally therein in a direction generally orthogonal to the peg, the bore being sized and shaped for receiving a fastener inserted in an olecranon process of the ulna generally transverse to the longitudinal axis of the ulna to secure the radioulnar component to the ulna,
    wherein the humeral component has a bore extending axially through the spool for receiving at least one fastener to attach the humeral component to the humerus, at least a portion of the bore being completely surrounded by the spool, the humeral component being free of a stem for extending into a medullary canal of the humerus.

11. A prosthetic elbow as set forth in claim 10 wherein the humeral component further comprises a stabilizer for engaging the humerus for fixation and preventing rotation of the spool about the bore.

12. A prosthetic elbow as set forth in claim 11 wherein the stabilizer comprises a peg extending from the spool in a generally axial direction for engaging the humerus for fixation and preventing rotation of the spool about the bore.

13. A prosthetic elbow as set forth in claim 11 wherein the stabilizer comprises a panel extending from the spool in a generally axial direction for engaging the humerus for fixation and preventing rotation of the spool about the bore.

14. A prosthetic elbow as set forth in claim 13 wherein the stabilizer further comprises another panel extending from the spool in a generally axial direction for engaging the humerus for fixation and preventing rotation of the spool about the bore.

15. A prosthetic elbow as set forth in claim 14 wherein each of the panels has at least one cleat for attaching the humeral component to the humerus.

16. A prosthetic elbow as set forth in claim 10 wherein the spool has a cavity for receiving bone.

* * * * *